United States Patent [19]

Harrison

[11] Patent Number: Plant 7,653

[45] Date of Patent: Sep. 17, 1991

[54] ZANTEDESCHIA PLANT 'APRICOT GLOW'

[75] Inventor: Richmond E. Harrison, Palmerston North, New Zealand

[73] Assignee: Manukau Horticulture Limited, Auckland, New Zealand

[21] Appl. No.: 415,860

[22] Filed: Oct. 2, 1989

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Young & Thompson

[57] ABSTRACT

A new and distinct variety of Zantedeschia plant is disclosed, said plant being a seedling selection based on parent varieties *Zantedeschia elliottiana* and *Zantedeschia rehmannii.*

1 Drawing Sheet

The present invention relates to a new variety of Zantedeschia plant called Apricot Glow which the inventor has produced in the course of his studies and research aimed at finding new products capable of increasing the profits of horticulturists, either by readier sales or by greater productivity of the plants.

The new variety which is the object of the present invention is different from all other Zantedeschia known heretofore, and constitutes, with respect to the latter, an improvement, both by the shape and the color of the plant and by the very high productivity of the plants.

The new variety which is the object of the present invention has been obtained by seedling selection based on a controlled crossing of parent varieties *Zantedeschia elliottiana* and *Zantedeschia rehmannii* at Palmerston North, New Zealand. The seed parent is believed to be *Zantedeschia elliottiana*, and the pollen parent *Zantedeschia rehmannii.*

As a result, the new variety constitutes a new product adapted to be commercially cultured for the production of flowering pot plants.

The new variety which is the object of the present invention has been asexually reproduced by division and by tissue culture in a laboratory at Auckland, New Zealand. Each generation of new plants so produced has been identical to the original selection in all distinguishing characteristics, establishing that the variety is stable.

The plant described in the description which follows has been cultivated under glass.

BRIEF DESCRIPTION OF THE DRAWING

The drawing shows the plant in bloom.

The identification of the colors of the description was made in accordance with the tables of "The Royal Horticultural Society Colour Chart" of London. (Indicated in the text by the initials R.H.S., followed by the number of the table.

DESCRIPTION

PLANT

Origin: Unknown hybrid of *Zantedeschia spp.*

Vegetative Carriage: Robust plant, multi branched leaves and stems.

Length: From the base of the spathe 20 cm.

Roots; Originate from the upper surface of the tuber, thin, numerous roots, 10-15 cm long.

Floral Stems: Stem number depends of tuber size, averaging 3-6, emerging from the base of the plant, straight, upright, rigid.

*Carriage.*—Upright.

*Dimensions.*—Average length 15-20 cm. Average diameter 5-8 mm.

*Nodes*—Clustered on the top surface of the tuber.

*Surface.*—Semi-Glossy.

*Color.*—Green (R.H.S. 141-A-B).

Leaves: Usually numerous, emerging from the base of the plant having a short peduncle up to 3-6 cm, rigid.

*Border.*—A single lance-shaped form, wavy edge tapering to a sharp point.

*Texture.*—Herbaceous, thick.

*Surface.*—Upper surface semi glossy, glabrous, with veins, plunging into the limb. Lower surface opaque. No white spotting on either surface.

*Color.*—Upper surface mid to dark green (R.H.S. 131 B). Lower surface lighter green (R.H.S. 143 B-C).

*Dimensions.*—Peduncle, length 3-6 cm, diameter 2-5 mm. Limb, length 10-12 cm, width 4-8 cm.

Spathe (flower): Upright, terminal on the floral stem.

*Furled spathe.*—Of medium dimensions, rolled cylindrical.

*Dimensions.*—Length 4-8 cm diameter 4-6 cm.

*Color.*—At the opening edges of the spathe, pink-red blush (R.H.S. 53 B-C). Remainder of spathe Yellow Orange Blush. Background color (R.H.S. 13 B-C). Very light over blush (R.H.S. 53 B-C).

*Shape.*—Spathe is trumpet shaped, not cylindrical, opening to a sharp tip, with point.

*Texture.*—Thick.

*Surface.*—Smooth, not shiny.

REPRODUCTIVE ORGANS

Spadix: In center of spathe, cylinderical in shape arising from the floral stem terminal, surrounded by the spathe. Contains both male and female productive parts. Ovary at base. Stamen at top. Yellow in color (R.H.S. 13 B-C).

Odor: None.

Resistance to disease: Very good.

Resistance to transport: Very good.

Durability of the cut flower: Very good.

Flowering: Very abundant, long flowering period 4-6 weeks.

What is claimed is:

1. A new and distinct variety of Zantedeschia plant, said plant being a seedling resulting from a controlled cross between *Zantedeschia elliottiana* and *Zantedeschia rehmannii*, substantially as described and illustrated.

* * * * *

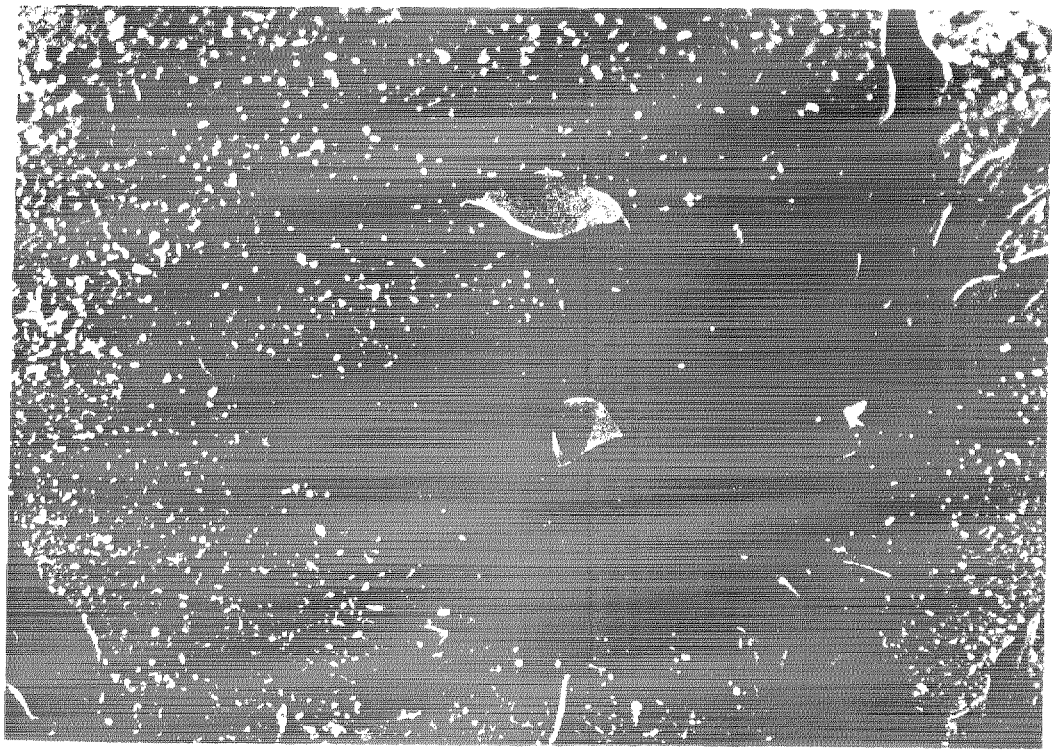

PLT-263 SR
C5203 OR PP 007,653